United States Patent
Evans et al.

(10) Patent No.: US 7,102,022 B2
(45) Date of Patent: Sep. 5, 2006

(54) METHOD FOR THE START-UP OF AN EPOXIDATION PROCESS AND A PROCESS FOR THE EPOXIDATION OF AN OLEFIN

(75) Inventors: Wayne Errol Evans, Richmond, TX (US); John Robert Lockemeyer, Sugar Land, TX (US); Dominicus Maria Rekers, Amsterdam (NL); Arend Jan Te Raa, The Hague (NL); Thijs Wermink, The Hague (NL)

(73) Assignee: Shell Oil Company, Houston, TX (US)

( * ) Notice: Subject to any disclaimer, the term of this patent is extended or adjusted under 35 U.S.C. 154(b) by 80 days.

(21) Appl. No.: 10/607,346

(22) Filed: Jun. 26, 2003

(65) Prior Publication Data

US 2004/0110971 A1 Jun. 10, 2004

Related U.S. Application Data

(60) Provisional application No. 60/392,679, filed on Jun. 28, 2002.

(51) Int. Cl.
*C07D 301/10* (2006.01)

(52) U.S. Cl. .................................................. 549/536
(58) Field of Classification Search .................. 549/536
See application file for complete search history.

(56) References Cited

U.S. PATENT DOCUMENTS

| | | | |
|---|---|---|---|
| 2,219,575 A | 10/1940 | McNamee et al. | 260/348 |
| 4,007,135 A | 2/1977 | Hayden et al. | 252/467 |
| 4,389,338 A | 6/1983 | Mitsuhata et al. | 252/463 |
| 4,761,394 A | 8/1988 | Lauritzen | 502/348 |
| 4,766,105 A | 8/1988 | Lauritzen | 502/216 |
| 4,822,900 A | 4/1989 | Hayden | 549/534 |
| 4,845,296 A | 7/1989 | Ahmed et al. | 564/477 |
| 4,874,879 A | 10/1989 | Lauritzen et al. | 549/536 |
| 5,100,859 A | 3/1992 | Gerdes et al. | 502/439 |
| 5,102,848 A | 4/1992 | Soo et al. | 502/218 |
| 5,155,242 A | 10/1992 | Shankar et al. | 549/534 |
| 5,380,697 A | 1/1995 | Matusa et al. | 502/348 |
| 5,395,812 A | 3/1995 | Nagase et al. | 502/238 |
| 5,407,888 A | 4/1995 | Herzog et al. | 502/317 |
| 5,444,034 A | 8/1995 | Rizkalla | 502/347 |
| 5,504,052 A | 4/1996 | Rizkalla et al. | 502/347 |
| 5,646,087 A | 7/1997 | Rizkalla et al. | 502/347 |
| 5,736,483 A | 4/1998 | Rizkalla | 502/347 |
| 5,739,075 A | 4/1998 | Matusa | 502/302 |
| 5,770,746 A | 6/1998 | Cooker et al. | 549/534 |
| 5,780,656 A | 7/1998 | Rizkalla et al. | 549/534 |
| 5,801,259 A | 9/1998 | Kowaleski | 549/536 |
| 5,854,167 A | 12/1998 | Rizkalla et al. | 502/347 |
| 6,087,299 A | 7/2000 | Grub et al. | 502/347 |
| 6,368,998 B1 | 4/2002 | Lockemeyer | 502/347 |
| 6,372,925 B1 | 4/2002 | Evans et al. | 549/536 |
| 6,511,938 B1 | 1/2003 | Liu et al. | 502/347 |
| 6,579,825 B1 | 6/2003 | Lockemeyer | 502/347 |
| 6,656,874 B1 | 12/2003 | Lockemeyer | 502/347 |
| 6,750,173 B1 | 6/2004 | Rizkalla et al. | 502/348 |
| 6,762,311 B1 | 7/2004 | Rizkalla et al. | 549/534 |
| 2002/0010094 A1 | 1/2002 | Lockemeyer | 502/439 |

FOREIGN PATENT DOCUMENTS

| | | |
|---|---|---|
| EP | EPA-3642 | 8/1979 |
| EP | 0266015 | 5/1988 |
| EP | 326392 | 8/1989 |
| EP | 352849 | 1/1990 |
| EP | EPA-352850 | 1/1990 |
| EP | 567273 | 10/1993 |
| EP | EPA-716884 | 6/1996 |
| EP | 0933130 | 8/1999 |
| EP | 1 002 575 A2 | 5/2000 |
| GB | 1170663 | 11/1969 |
| GB | 1191983 | 5/1970 |
| GB | 1489335 | 10/1977 |
| WO | 95/05896 | 3/1995 |
| WO | 95/17957 | 7/1995 |
| WO | WO 96/04989 | 2/1996 |
| WO | 00/15332 | 3/2000 |
| WO | 00/15333 | 3/2000 |
| WO | 00/15334 | 3/2000 |
| WO | 00/15335 | 3/2000 |
| WO | WO 01/96324 | 12/2001 |
| WO | 2004002972 | 1/2004 |
| WO | 04/092148 | 10/2004 |

OTHER PUBLICATIONS

Kirk–Othmer's Encyclopedia of Chem. Tech., $3^{rd}$ Ed., vol. 9, pp. 445–447.(1980).
Brunauer, Emmet and Teller in J. American Chemical Society. vol. 60 (1938). pp. 309–316.
U.S.P.T.O. Office Action for Application Ser. No. 10/606,440 (TH1808), mailed Aug. 18, 2005.
International Preliminary Examination Report, dated Oct. 5, 2004, for PCT/US2003/20095 (TH2202 PCT) .
Written Opinion, dated Mar. 16, 2004, for PCT/US2003/20095 (TH2202 PCT) .
International Search Report, dated Jun. 11, 2004, for PCT/US2003/19827 (TH1808 PCT) .

(Continued)

*Primary Examiner*—Taofiq Solola (57) ABSTRACT

A method for the start-up of a process for the epoxidation of an olefin, which method comprises
contacting a catalyst bed comprising a silver-based highly selective epoxidation catalyst, or a precursor of the catalyst comprising the silver in cationic form, with a feed comprising oxygen at a temperature of the catalyst bed above 260° C. for a period of at most 150 hours, and
subsequently decreasing the temperature of the catalyst bed to a value of at most 260° C., and a process for the epoxidation of an olefin, which process, comprises
contacting a catalyst bed comprising a silver-based highly selective epoxidation catalyst, or a precursor of the catalyst comprising the silver in cationic form, with a feed comprising oxygen at a temperature of the catalyst bed above 260° C. for a period of at most 150 hours, and
subsequently decreasing the-temperature of the catalyst bed to a value of at most 260° C. and contacting the catalyst with the feed comprising the olefin and oxygen.

35 Claims, 1 Drawing Sheet

OTHER PUBLICATIONS

International Preliminary Examination Report, dated Oct. 27, 2004, for PCT/US2003/19827 (TH1808 PCT).

Written Opinion, dated Jul. 16, 2004, for PCT/US2003/19827 (TH1808 PCT).

International Search Report, dated Oct. 30, 2003, for PCT/US2003/19828 (WO04/002971) (TH2305 PCT).

International Preliminary Examination Report, dated Oct. 10, 2004, for PCT/US2003/19828 (WO04/002971) (TH2305 PCT).

Written Opinion, dated May 6, 2004, for PCT/US2003/19828 (WO04/002971) (TH2305 PCT).

International Search Report, dated Jan. 18, 2005, for PCT/US2004/010457 (WO 2004/092148) (TH2467 PCT).

Written Opinion, dated Jan. 18, 2005, for PCT/US2004/010457 (WO 2004/092148) (TH2467 PCT).

International Preliminary Report on Patentability, dated Aug. 18, 2005, for PCT/US2004/010457 (WO 2004/092148) (TH2467 PCT).

U.S.P.T.O. Office Action for Application Ser. No. 10/816,480 (TH2467), mailed Jun. 23, 2005.

Beilstein Institute for Organic Chemistry. Frankfurt–Main. DE. XP002296657. J. Am. Chem. Society. vol. 56. (1934): pages 1870–1872.

Figure 1.

METHOD FOR THE START-UP OF AN EPOXIDATION PROCESS AND A PROCESS FOR THE EPOXIDATION OF AN OLEFIN

This application claims the benefit of U.S. Provisional Application No. 60/392,679 filed Jun. 28, 2002 the entire disclosure of which is hereby incorporated by reference.

FIELD OF THE INVENTION

The invention relates to a method for the start-up of a process for the epoxidation of an olefin, which process employs a silver-based highly selective epoxidation catalyst. The invention also relates to a process for the epoxidation of an olefin, which process includes the start-up method of this invention.

BACKGROUND OF THE INVENTION

The catalytic epoxidation of olefins over silver-based catalysts, yielding the corresponding olefin oxide, has been known for a long time. Conventional silver-based catalysts have provided the olefin oxides with notoriously low selectivity. For example, when using conventional catalysts in the epoxidation of ethylene, the selectivity towards ethylene oxide, expressed as a fraction of the ethylene converted, does not reach values above the 6/7 or 85.7 mole-% limit. Therefore, this limit has long been considered to be the theoretically maximal selectivity of this reaction, based on the stoichiometry of the reaction equation $7C_2H_4 + 6O_2 => 6C_2H_4O + 2CO_2 + 2H_2O$, cf. Kirk-Othmer's *Encyclopedia of Chemical Technology*, $3^{rd}$ ed., Vol. 9, 1980, p. 445.

The selectivity determines to a large extent the economical attractiveness of an epoxidation process. For example, one percent improvement in the selectivity of the epoxidation process can reduce the yearly operating costs of a large scale ethylene oxide plant substantially.

The olefin oxide produced by the epoxidation process may be reacted with water, an alcohol or an amine to form a 1,2-diol, a 1,2-diol ether or an alkanolamine. Thus, 1,2-diols, 1,2-diol ethers and alkanolamines may be produced in a multi-step process comprising olefin epoxidation and converting the formed olefin oxide with water, an alcohol or an amine. Any improvement in the selectivity of the epoxidation process can also reduce the yearly operating costs in the overall process for the production of a 1,2-diol, a 1,2-diol ether or an alkanolamine.

Modern silver-based epoxidation catalysts are highly selective towards olefin oxide production. When using the modern catalysts in the epoxidation of ethylene the selectivity towards ethylene oxide can reach values above the 6/7 or 85.7 mole-% limit referred-to. Such highly selective catalysts comprise, in addition to silver, a selectivity enhancing dopant which may be selected from rhenium, molybdenum, tungsten and nitrate- or nitrite-forming compounds, cf. for example U.S. Pat. No. 4,761,394 and U.S. Pat No. 4,766,105.

A reaction modifier, for example an organic halide, may be added to the feed to an epoxidation process for increasing the selectivity (cf. for example EP-A-352850, U.S. Pat. No. 4,761,394 and U.S. Pat. No. 4,766,105, which are herein incorporated by reference). The reaction modifier suppresses the undesirable oxidation of olefin or olefin oxide to carbon dioxide and water, relative to the desired formation of olefin oxide, by a so-far unexplained mechanism. EP-A-352850 teaches that there is an optimum in the selectivity as a function of the concentration of organic halide in the feed, at a constant oxygen conversion level and given set of reaction conditions.

During the initial phase of an epoxidation process, the catalyst experiences the so-called "break-through phase" during which the oxygen conversion is very high, the selectivity is very low, even in the presence of a reaction modifier, and the epoxidation process is difficult to control. It might take a long time in the start-up of a commercial epoxidation process for the conversion to drop so that the reaction can more easily be controlled at an attractive level of the selectivity. It goes without saying that there is an economical incentive to shorten the start-up period and make the catalyst operate at a high selectivity with a minimum delay.

U.S. Pat. No. 5,155,242 relates to the start-up of an epoxidation process wherein a conventional catalyst is employed. In this patent document there is disclosed an improved start-up procedure wherein the conventional catalyst is subjected to a pre-soak period in the presence of the organic halide at a temperature less than the operating temperature of the reactor.

U.S. Pat. No. 4,874,879 relates to the start-up of an epoxidation process wherein a highly selective catalyst is employed. In this patent document there is disclosed an improved start-up procedure wherein the highly selective catalyst is subjected to a pre-soak period in the presence of the organic halide at a temperature less than the operating temperature of the reactor. This procedure may alleviate to some extent the problems associated with the duration of the start-up. However, it has been experienced that, still, it takes several days for the catalyst to pass through the break-through phase. This results in considerable losses of olefin oxide production, as described hereinbefore.

WO-95/05896 proposes a silver-based catalyst which comprises, as a further component, a selected quantity of chloride. Such catalysts have improved start-up characteristics over catalysts which do not comprise chloride.

SUMMARY OF THE INVENTION

The present invention provides a method for the start-up of a process for the epoxidation of an olefin, which method comprises contacting a catalyst bed comprising a silver-based highly selective epoxidation catalyst, or a precursor of the catalyst comprising the silver in cationic form, with a feed comprising oxygen at a temperature of the catalyst bed above 260° C. for a period of at most 150 hours, and subsequently decreasing the temperature of the catalyst bed to a value of at most 260° C.

In preferred embodiments of this invention, amongst others, the start-up method is a part of an epoxidation process. In such embodiments the present invention also provides a process for the epoxidation of an olefin, which process comprises contacting a catalyst bed comprising a silver-based highly selective epoxidation catalyst, or a precursor of the catalyst comprising the silver in cationic form, with a feed comprising oxygen at a temperature of the catalyst bed above 260° C. for a period of at most 150 hours, and subsequently decreasing the temperature of the catalyst bed to a value of at most 260° C. and contacting the catalyst with the feed comprising the olefin and oxygen.

The invention also provides a process for producing a 1,2-diol, 1,2-diol ether, or an alkanolamine, comprising converting an olefin oxide into the 1,2-diol, the 1,2-diol ether, or the alkanolamine, wherein the olefin oxide has been obtained by a process for the epoxidation of an olefin according to this invention.

DETAILED DESCRIPTION OF THE INVENTION

In accordance with this invention, the start-up of an epoxidation process wherein a highly selective catalyst is employed can be improved considerably by subjecting the catalyst during the break-through phase to a feed comprising oxygen at a temperature above 260° C. This reduces the duration of the start-up procedure, typically from days to hours, while during the break-through phase in the additional presence of the olefin, the catalyst is able to produce the olefin oxide at a high selectivity. Further, during the break-through phase at above 260° C. in the presence of oxygen the selectivity of the catalyst increases. Further, there is no longer a need of a pre-soak period, so that the operation in the start-up becomes less complicated.

These findings are unexpected in the light of the prior art, which teaches that high catalyst temperatures are generally to be avoided, as occurrences of a high temperature lead to high oxygen conversions, low selectivities, operation difficulties and short catalyst life. U.S. Pat. No. 5,646,087 teaches to avoid the presence of oxygen when a silver-based catalyst is exposed to a high temperature, and a belief is expressed that at temperatures of 250° C. and higher oxygen is absorbed in substantial quantities into the bulk of the silver where it has an adverse effect on the catalyst characteristics. WO-95/05896 teaches that a very high oxygen conversion provides for a very "hot" start-up which is more difficult to control. U.S. Pat. No. 5,155,242 teaches that extremely high oxygen conversions can result in hot spots in the catalyst, which can decrease its life due to sintering.

The Example of U.S. Pat. No. 4,874,879 relates to the start-up of a commercial scale epoxidation process. In this Example the reactor coolant temperature was initially at a temperature of 450° F. (232° C.), later at 480° F. (249° C.) The observed maximum catalyst temperature of 525° F. (274° C.), as disclosed, is in all likelihood the temperature of only a small portion of the catalyst bed (i.e. a local "hot spot", of which the occurrence immediately after initiation of the epoxidation is a well known phenomenom). The relatively low coolant temperature ensures that this was a short duration temperature excursion and that the catalyst bed as a whole did not experience the temperature excursion.

Although the invention may be practiced in many ways, it is preferred to practice it as a gas phase process, i.e. a process in which the feed is contacted in the gas phase with the catalyst which is present as a solid material, typically in a packed bed positioned in a reactor, which may be a tubular reactor. Frequently, in commercial scale operation, the process of the invention may involve a quantity of catalyst which is at least 10 kg, for example at least 20 kg, frequently in the range of from $10^2$ to $10^7$ kg, more frequently in the range of from $10^3$ to $10^6$ kg. Generally the process is carried out as a continuous process. The reactor is typically equipped with heat exchange facilities to heat or cool the catalyst. As used herein, the feed is considered to be the composition which is contacted with the catalyst. As used herein, the catalyst temperature or the temperature of the catalyst bed is deemed to be the weight average temperature of the catalyst particles.

As used herein, a highly selective silver-based catalyst is generally a catalyst which, when operated fresh, can exhibit in the gas phase epoxidation of ethylene a theoretical selectivity at zero oxygen conversion, $S_0$, of at least 6/7 or 85.7%. More in particular, this theoretical selectivity can be accomplished at a reaction temperature of 260° C. The value of $S_0$ for a given catalyst is found by operating the catalyst, in particular at a temperature of 260° C., in a range of gas hourly space velocities, resulting in a range of selectivity values and oxygen conversion values corresponding to the range of gas hourly space velocities employed. The selectivity values found are then extrapolated back to the theoretical selectivity at zero oxygen conversion, $S_0$. As used herein, the selectivity is, the fraction of the converted olefin yielding the olefin oxide.

Generally, the highly selective silver-based catalyst is a supported catalyst. The support may be selected from a wide range of inert support materials. Such support materials may be natural or artificial inorganic materials and they include silicon carbide, clays, pumice, zeolites, charcoal and alkaline earth metal carbonates, such as calcium carbonate. Preferred are refractory support materials, such as alumina, magnesia, zirconia and silica. The most preferred support material is α-alumina.

The support material is preferably porous and has preferably a surface area, as measured by the B.E.T. method, of at most 20 $m^2/g$ and in particular from 0.05 to 20 $m^2/g$. More preferably the B.E.T. surface area of the support is in the range of 0.1 to 10, in particular from 0.1 to 3.0 $m^2/g$. As used herein, the B.E.T. surface area is deemed to have been measured by the method as described in Brunauer, Emmet and Teller in *J. Am. Chem. Soc.* 60 (1938) 309–316.

Generally, the highly selective silver-based catalysts comprise, in addition to silver, a Group IA metal, and one or more selectivity enhancing dopants selected from rhenium, molybdenum, and tungsten. Silver is suitable present in a quantity of from 10 to 500 g/kg on the total catalyst. The Group IA metals, as well as the selectivity enhancing dopants, may each be present in a quantity of from 0.01 to 500 mmole/kg, calculated as the element (rhenium, molybdenum, tungsten, or Group IA metal) on the total catalyst. Preferably, the Group IA metal is selected from lithium, potassium, rubidium and cesium. Rhenium, molybdenum, or tungsten may suitably be provided as an oxyanion, for example, as a perrhenate, molybdate, or tungstate, in salt or acid form.

It is preferred to avoid a high silver density on the surface of the highly selective catalyst, i.e. the quantity of silver related to the surface area of the support, in order to diminish contact sintering of the silver. Without wishing to be bound by theory, it is believed that contact sintering of the silver on the catalyst surface may occur when the catalyst is exposed to high temperature, which leads to a reduction in the catalyst's lifetime. Typically the quantity of silver relative to the surface area of the support is at most 0.22 $g/m^2$, more typically at most 0.2 $g/m^2$. In the normal practice of this invention, the quantity of silver relative to the surface area of the support is frequently at least 0.01 $g/m^2$, more frequently at least 0.02 $g/m^2$.

Of special preference are the silver-based catalysts which comprise rhenium, in addition to silver. Such catalysts are known from U.S. Pat. No. 4,761,394 and U.S. Pat. No. 4,766,105, which are incorporated herein by reference.

Broadly, they comprise silver, rhenium or compound thereof, a further metal or compound thereof and optionally a rhenium co-promoter which may be selected from one or more of sulfur, phosphorus, boron, and compounds thereof, on the support material. More specifically the further metal is selected from the group of Group IA metals, Group IIA metals, molybdenum, tungsten, chromium, titanium, hafnium, zirconium, vanadium, thallium, thorium, tantalum, niobium, gallium and germanium and mixtures thereof. Preferably the further metal is selected from the Group IA metals such as lithium, potassium, rubidium and cesium and/or from the Group IIA metals such as calcium and barium. Most preferably it is lithium, potassium and/or cesium. Where possible, rhenium, the further metal or the rhenium co-promoter is provided as an oxyanion, in salt or acid form.

Preferred amounts of the components of these catalysts are, when calculated as the element on the total catalyst:
silver from 10 to 500 g/kg,
rhenium from 0.01 to 50 mmole/kg,
the further metal or metals from 0.1 to 500 mmole/kg each, and, if present,
the rhenium co-promoter or co-promoters from 0.1 to 30 mmole/kg each.

The preparation of the catalysts is known in the art and the known methods are applicable to this invention. Methods of preparing the catalyst include impregnating the support with a silver compound and with other catalyst ingredients, and performing a reduction to form metallic silver particles. Reference may be made, for example, to U.S. Pat. No. 4,761,394, U.S. Pat. No. 4,766,105, U.S. Pat. No. 5,380,697, U.S. Pat. No. 5,739,075, U.S. Pat. No. 6,368,998B1, US-2002/0010094 A1, WO-00/15333, WO-00/15334 and WO-00/15335, which are incorporated herein by reference. Suitable catalysts for use in this invention are, for example, the S-879, S-881 and S-882 catalysts, commercially available from CRI Catalyst Company.

This invention may be applied to new catalysts, as well as to aged catalysts which, due to a plant shutdown, have been subjected to a prolonged shut-in period.

The invention may also be applied to a precursor of the catalyst. By a precursor of the catalyst is meant the supported composition which comprises the silver in unreduced, i.e. cationic form, and which further comprises the components necessary for obtaining after reduction the intended highly selective catalyst. In this case, the reduction will be effected during the contacting with the feed comprising oxygen at a temperature above 260° C.

The olefin for use in the epoxidation process may be any olefin, such as an aromatic olefin, for example styrene, or a di-olefin, whether conjugated or not, for example 1,9-decadiene or 1,3-butadiene. Typically, the olefin is a monoolefin, for example 2-butene or isobutene. Preferably, the olefin is a mono-α-olefin, for example 1-butene or propylene. The most preferred olefin is ethylene.

The epoxidation process may be air-based or oxygen-based, see Kirk-Othmer's *Encyclopedia of Chemical Technology*, 3rd ed., Vol. 9, 1980, p. 445–447. In the air-based process air or air enriched with oxygen is employed as the source of the oxidizing agent while in the oxygen-based processes high-purity (>95 mole-%) oxygen is employed as the source of the oxidizing agent. Presently most epoxidation plants are oxygen-based and this is a preferred embodiment of the present invention.

Oxygen is typically applied at a concentration which avoids the flammable regime. The concentration of oxygen in the feed may be adjusted as the concentration of the olefin is changed so as to remain outside the flammable regime. The actual safe operating ranges depend, along with the feed composition, also on the epoxidation conditions such as the catalyst temperature and the pressure.

The organic halide, as the reaction modifier, is in particular an organic bromide, and more in particular an organic chloride. Preferred organic halides are chlorohydrocarbons or bromohydrocarbons. More preferably they are selected from: the-group of methyl chloride, ethyl chloride, ethylene, dichloride, ethylene dibromide, vinyl chloride or a mixture thereof. Most preferred reaction modifiers are ethyl chloride and ethylene dichloride.

Although the organic halide may be supplied as a single compound, upon contact with the catalyst a variety of compounds may be formed which function as reaction modifier, and which may be present in the feed if a recycle is applied. For example, when applying ethyl chloride in an ethylene oxide process, the feed may in practice comprise ethyl chloride, vinyl chloride, ethylene dichloride and methyl chloride.

In preferred embodiments, organic halide is employed as the single reaction modifier. In other embodiments, nitrate- or nitrite-forming compounds, e.g. nitrogen oxides and/or organic nitrogen compounds, are used as reaction modifier together with the organic halide, in particular an organic chloride. Suitable nitrogen oxides are of the general formula $NO_x$ wherein x, which denotes the ratio of the number of oxygen atoms to the number of nitrogen atoms, is in the range of from 1 to 2. These nitrogen oxides include for example NO, $N_2O_3$ and $N_2O_4$. Suitable organic nitrogen compounds are nitro compounds, nitroso compounds, amines, nitrates and nitrites, for example nitromethane, 1-nitropropane or 2-nitropropane. Hydrazine, hydroxylamine or ammonia may be employed as well. It is frequently considered that under the operating conditions of olefin epoxidation the nitrogen containing reaction modifiers are precursors of nitrates or nitrites, i.e. they are so-called nitrate- or nitrite-forming compounds (cf. e.g. EP-A-3642, U.S. Pat. No. 4,822,900, which are incorporated herein by reference).

The feed may contain one or more optional components, such as carbon dioxide, inert gases and saturated hydrocarbons. Carbon dioxide is a by-product in the epoxidation process. However, carbon dioxide generally has an adverse effect on the catalyst activity, and high concentrations of carbon dioxide are therefore typically avoided. The inert gas may be, for example, nitrogen or argon, or a mixture thereof. Suitable saturated hydrocarbons are propane and cyclopropane, and in particular methane and ethane. Saturated hydrocarbons may be added to the feed in order to increase the oxygen flammability limit.

When new catalysts are utilised, it may be useful in some instances to pretreat these catalysts prior to carrying out the start-up method by subjecting them to a high temperature with a sweeping gas passing over the catalyst. The sweeping gas is typically an inert gas, for example nitrogen or argon, or mixtures comprising nitrogen and/or argon. The high catalyst temperature converts a significant portion of organic nitrogen compounds which may have been used in the manufacture of the catalysts to nitrogen containing gases which are swept up in the gas stream and removed from the catalyst. In addition, any moisture may be removed from the catalyst. Typically, when the catalyst is loaded in the reactor, by utilizing the coolant heater, the temperature of the catalyst is brought up to 200 to 250° C. and the gas flow is passed over the catalyst. The start-up of used catalysts may or may not require the use of a sweeping gas, but it may frequently be used. Further details on these procedures may be found in U.S. Pat. No. 4,874,879, which is incorporated herein by reference.

As indicated hereinbefore, the practice of this invention involves the step of contacting the catalyst with a feed comprising oxygen at a temperature above 260° C. This step may be considered the break-through phase of the process, and, for the sake of clarity only, this step of the process will be indicated hereinafter by the term "break-through phase". Typically, the temperature of the catalyst is at most 300° C., preferably in the range of from 260 to 290° C., more preferably from 265 to 280° C. Typically, the catalyst temperature above 260° C. may be maintained for a period of from 0.25 to 100 hours, preferably from 0.5 to 40 hours, more preferably from 1 to 30 hours, in particular from 2 to 20 hours, for example less than 10 hours. In general, a relatively short period is preferred, as this will shorten the time involved in the start-up method, and it also tends to result in the catalyst being more active after the break-through phase.

The feed which may be employed in the break-through phase may be any oxygen containing feed, which may be pure oxygen or it may comprise additional components which are inert or non-inert under the prevailing conditions. Suitably, the feed is a mixture of oxygen with an inert gas, such as argon, helium, and nitrogen, or a saturated hydrocarbon. Such mixtures may be, for example, air, oxygen enriched air, or air/methane mixtures. The quantity of oxygen in the feed is preferably in the range of from 0.5 to 30% v, in particular from 1 to 25% v, more in particular 1.5 to 15% v, relative to the total feed. The inert and non-inert components may be selected amongst those which may be components of the feed of an epoxidation process as described hereinbefore, and the quantities in which they may be present may be in the ranges as described hereinafter. For example, the feed may comprise an olefin, in which case the olefin will at least partly be converted into the corresponding epoxide. This is advantageous as it yields valuable product and the heat of formation of the olefin oxide may assist in accomplishing and controlling the desired temperature. Another advantage of having an olefin present in the break-through phase is that the improvement in selectivity of the catalyst may be monitored by monitoring the rate of conversion of the olefin: for example, in a continuous process a stabilization of a declining rate indicates that the selectivity improvement is near completion.

Thus, during the break-through phase the feed may comprise, in addition to oxygen, one or more components selected from the olefin, carbon dioxide, the inert gases and reaction modifiers, such as organic halides, optionally in the additional presence of nitrate- or nitrite-forming compounds. However, the presence of one or more of these additional components in the feed during the break-through phase is not considered to be essential to the invention.

During the break-through phase, the reactor inlet pressure is typically at most 2500 kPa absolute. The reactor inlet pressure is typically at least 1000 kPa absolute. "GHSV" or Gas Hourly Space Velocity is the unit volume of gas at normal temperature and pressure (0° C., 1 atm, i.e. 101.3 kPa) passing over one unit volume of packed catalyst per hour. Preferably, when the invention is practiced as a gas phase process involving a packed catalyst bed, the GHSV is in the break-through phase in the range of from 500 to 10000 Nl/(l.h).

In a particular embodiment, amongst others, the start-up-method may include prior to the break-through phase several steps, as follows. Firstly, the catalyst may be contacted with the feed comprising the olefin and optionally a saturated hydrocarbon, in particular ethylene and optionally methane, at a temperature of at most 260° C. preferably at a temperature in the range of from 200 to 250° C. The organic halide may than be added to the feed. Subsequently oxygen may be added to the feed. Within a few minutes of the addition of oxygen the epoxidation reaction may initiate. Typically, all of the catalyst may be contacted with the organic halide before the oxygen is added to the feed. This means that, when the catalyst is applied as a packed bed positioned in a reactor, it is sufficient that organic halide is detected in the reactor outlet stream before the oxygen is added to the feed. In a preferred embodiment, oxygen may be added to the feed simultaneously with the organic halide, which practically eliminates the pre-soak period and makes the start-up method shorter and less complicated.

In this stage of the particular embodiment of the previous paragraph, with the olefin, the saturated hydrocarbon (optional), the organic halide and oxygen being added to the feed, the feed comprises typically the olefin in a quantity of from 5 to 70 mole-%, more typically from 10 to 50 mole-%; the saturated hydrocarbon in a quantity of from 0 to 70 mole-%, more typically from 10 to 60 mole-%; and oxygen in a quantity of from 0.5 to 15 mole-%, more typically from 1 to 12 mole-%. It may be advantageous to apply prior to and during the break-through phase a lower oxygen concentration and a lower olefin concentration in the feed, compared with the feed composition in later stages of the process during normal olefin oxide production. Lower oxygen concentration and a lower olefin concentration in the feed will reduce the oxygen conversion level so that, advantageously, hot spots in the catalyst are better avoided and the process will be more easily controllable. The concentration of organic halide in the feed is typically maintained at from $0.05 \times 10^{-4}$ to $50 \times 10^{-4}$ mole-%, in particular from $0.2 \times 10^{-4}$ to $30 \times 10^{-4}$ mole-%, in particular from $0.5 \times 10^{-4}$ to $20 \times 10^{-4}$ mole-%, calculated on the basis of the halogen content, relative to the total feed. The quantity of the organic halide in the feed may be expressed relative to the quantity of the hydrocarbon in the feed by the relative quantity Q, as explained hereinafter. Typically, the value of Q is in the range of from $0.2 \times 10^{-6}$ to $200 \times 10^{-6}$, in particular from $1 \times 10^{-6}$ to $100 \times 10^{-6}$, more in particular from $5 \times 10^{-6}$ to $60 \times 10^{-6}$. It is an advantage of this invention that the concentration of organic halide may be relatively high during the break-through phase, so that there may not be a need for changing the concentration when entering the break-through phase or leaving the break-through phase. For example, during the break-through phase the concentration of the organic halide may be at least $1 \times 10^{-4}$ mole-%, in particular from $1 \times 10^{-4}$ to $30 \times 10^{-4}$ mole-%, more in particular from $1.5 \times 10^{-4}$ to $20 \times 20^{-4}$ mole-%, calculated on the basis of the halogen content, relative to the total feed, in which case the value of Q may typically be at least $3 \times 10^{-6}$, in particular from $3 \times 10^{-6}$ to $10 \times 10^{-6}$, more in particular from $5 \times 10^{-6}$ to $60 \times 10^{-6}$.

After the break-through phase, the catalyst temperature is decreased to a value of at most 260° C. For the sake of clarity only, the phase of the epoxidation process after the break-through phase will be indicated herein by the term "post-break-through phase". In the post-break-through phase, the invention may be practiced by using methods known in the art of epoxidation processes. Reference may be made, for example to U.S. Pat. No. 4,761,394, U.S. Pat. No. 4,766,105, U.S. Pat. No. 6,372,925B1, U.S. Pat. No. 4,874,879 and U.S. Pat. No. 5,155,242, which are incorporated herein by reference.

Typically, during the post-break-through phase the catalyst temperature is in the range of from 180 to 260° C., more typically in the range of from 200 to 255° C. Such temperatures are in particular suitable as long as the catalyst has not yet substantially been subject to an aging-related performance decline. Such aging manifests itself by a reduction in the activity of the catalyst. When a reduction in activity of the catalyst is manifest, the catalyst temperature may be increased in order to compensate for the reduction in activity. The catalyst temperature may ultimately be increased to values above 260° C., for example up to a temperature of 325° C., typically in the range of from 270 to 300° C. Generally speaking, the catalyst temperature may be increased until it becomes undesirably high, at which point in time the catalyst is deemed to be at the end of its lifetime and would need to be exchanged.

In the post-break-through phase, the concentration of the components in the feed may be selected within wide ranges, as described hereinafter.

Typically, the olefin concentration in the feed is in the range of from 5 to 70 mole-%, in particular from 10 to 50 mole-%, relative to the total feed. If desired, the olefin concentration may be increased during the lifetime of the catalyst, by which the selectivity may be improved in an operating phase wherein the catalyst has aged (cf. U.S. Pat. No. 6,372,925B1, which is incorporated herein by reference).

Typically, the concentration of oxygen is within the range of from 1 to 15 mole-%, more typically from 2 to 12 mole-% of the total feed.

Typically, concentrations of carbon dioxide in the feed in excess of 20 mole-%, preferably in excess of 10 mole-%, more preferably in excess of 5 mole-%, relative to the total feed, are avoided during the epoxidation process and its start-up. A concentration of carbon dioxide as low as 1 mole-% or lower, relative to the total feed, may be employed. Inert gas may be present in the feed in a concentration of from 0.5 to 95 mole-%. In an air based process inert gas may be present in the feed in a concentration of from 30 to 90 mole-%, typically from 40 to 80 mole-%. In an oxygen based process inert gas may be present in the feed in a concentration of from 0.5 to 30 mole-%, typically from 1 to 15 mole-%. If saturated hydrocarbons are present, they may be present in a quantity of up to 70 mole-%, typically in a quantity in the range of from 10 to 60 mole-%, relative to the total feed.

The organic halides are generally effective as reaction modifier when used in low concentration in the feed, for example up to 0.1 mole-%, calculated on the basis of the halogen content, relative to the total feed, for example from $0.01\times10^{-4}$ to 0.01 mole-%. In particular when the olefin is ethylene, it is preferred that the organic halide is present in the feed at a concentration of from $0.05\times10^{-4}$ to $50\times10^{-4}$ mole-%, in particular from $0.2\times10^{-4}$ to $30\times10^{-4}$ mole-%, more in particular from $0.5\times10^{-4}$ to $20\times10^{-4}$ mole-%, calculated on the basis of the halogen content, relative to the total feed. The same quantities, but calculated on the basis of the nitrogen content, and ranges thereof, apply for nitrogen containing modifiers, if they are present.

The relative quantity Q of the reaction modifier is the ratio of the effective molar quantity of active species of the reaction modifier present in the feed to the effective molar quantity of hydrocarbons present in the feed, both molar quantities being expressed in the same units, for example as mole-%, based on the total-feed.

When the reaction modifier is a halogen compound, for the purpose of calculating the effective molar quantity of active species of the reaction modifier and the value of Q, the number of active species is deemed to be the number of halogen atoms present, and when the reaction modifier is a nitrate- of nitrite-forming compound, the number of active species is deemed to be the number of nitrogen atoms present. This implies, for example, that 1 mole of ethylene dichloride provides 2 moles of active species, i.e. all of the chlorine atoms present provide an active species. On the other hand, reaction modifiers which are methyl compounds, such as methyl chloride and methyl bromide, are less responsive and therefore from 2 to 5 moles, in particular from 2.5 to 3.5 moles, suitably 3 moles of the methyl compounds may be deemed to provide 1 mole of the active species. This number may be determined and verified by routine experimentation, and without wishing to be bound by theory—it is believed that this number is higher as the methyl compound in question has a lesser ability to split off the heteroatom in question (for example the halogen or nitrogen atom). Thus, for example, when the feed comprises $2\times10^{-4}$ mole-% of ethyl chloride, $3\times10^{-4}$ mole-% of vinyl chloride, $1\times10^{-4}$ mole-% of ethylene dichloride and $1.5\times10^{-4}$ mole-% of methyl chloride, the effective molar quantity of active species of the reaction modifier may be calculated to amount to $(2\times10^{-4}\times1)+(3\times10^{-4}\times1)+(1\times10^{-4}\times2)+(1.5\times10^{-4}\times\frac{1}{3})=7.5\times10^{-4}$ mole-%.

In other words, the effective molar quantity of active species of the reaction modifier present in the feed may be calculated by multiplying the molar quantity of each of the reaction modifiers present in the feed with a factor, and adding up the multiplication products, wherein each factor represents the number of active heteroatoms, in particular halogen atoms and/or nitrogen atoms, present per molecule of the reaction modifier in question, on the understanding that the factor for a reaction modifier which is a methyl compound may be in the range of from $\frac{1}{5}$ to $\frac{1}{2}$, more typically from $\frac{1}{3.5}$ to $\frac{1}{2.5}$, suitably $\frac{1}{3}$.

The hydrocarbons present in the feed comprise the olefin and any saturated hydrocarbon present. The hydrocarbons present in the feed are deemed to have the ability to remove/strip reaction modifier from the catalyst surface and the extent to which they have this ability may differ for the various hydrocarbons. In order to account for these differences (relative to ethylene), the molar quantity of each of the hydrocarbons present is multiplied with a factor, before the molar quantities are added up to calculate the effective molar quantity of the hydrocarbons. Herein, the factor of ethylene is 1, by definition; the factor for methane may be in the range of from 0.1 to 0.5, or lower, for example down to 0, more typically from 0.2 to 0.4; the factor for ethane may be in the range of from 50 to 150, more typically from 70 to 120; and the factor for higher hydrocarbons (i.e. having at least 3 carbon atoms) may be in the range of from 10 to 10000, more typically from 50 to 2000. Such factors may be determined and verified by routine experimentation, and— without wishing to be bound by theory—it is believed that the factor is higher as the hydrocarbon in question has a greater ability to form radicals. Suitable factors for methane, ethane, propane and cyclopropane, relative to ethylene, are 0.3, 85, 1000 and 60, respectively. As an example, when the feed comprises 30 mole-% ethylene, 40 mole-% of methane, 0.4 mole-% of ethane and 0.0001 mole-% of propane, the effective molar quantity of the hydrocarbons may be calculated to amount to $(30\times1)+(40\times0.3)+(0.4\times85)+(0.0001\times1000)=76.1$ mole-%.

It is noted that when ethylene oxide is produced from ethylene without further hydrocarbons being present, the effective molar quantity of the hydrocarbons equals the actual molar quantity, and that the addition of ethane or higher hydrocarbons to an ethylene feed contributes significantly to the effective molar quantity, whereas there is relatively little contribution from any methane added. In some embodiments, the factor for methane may be taken as 0, thus neglecting, for example for reasons of convenience, the influence of methane.

Eligible values of Q are at least $0.2 \times 10^{-6}$, in particular at least $1 \times 10^{-6}$, and more in particular at least $2 \times 10^{-6}$. Eligible values of Q are at most $200 \times 10^{-6}$, in particular at most $100 \times 10^{-6}$, and in more particular at most $60 \times 10^{-6}$.

At any moment of the post-break-through phase, the value of Q may be adjusted so as to achieve an optimal selectivity towards the olefin oxide formation. In practice, the value of Q may be adjusted by adjusting the quantity of the reaction modifier present in the feed, while not changing the hydrocarbon concentrations in the feed.

As indicated hereinbefore, in the post-break-through phase the catalyst temperature may be increased, for example, in order to compensate for a reduction in activity which is related to catalyst aging. Deviations from the optimum selectivity which would result from a change in temperature may be reduced or even prevented, by adjusting the value of Q proportionally with the change in catalyst temperature. So, when the catalyst temperature is changed from $T_1$ to $T_2$, the value of Q may be changed from $Q_1$ to substantially $Q_2$, according to the formula $$Q_2 = Q_1 + B(T_2 - T_1),$$

wherein B denotes a constant factor, in $(^\circ C.)^{-1}$, which is greater than 0. Suitable values of B may be determined and verified by routine experimentation. The value of B is typically in the range of from $0.01 \times 10^{-6}$, to $1 \times 10^{-6}$, in particular from $0.1 \times 10^{-6}$ to $0.5 \times 10^{-6}$. A suitable value of B amounts to $0.22 \times 10^{-6}$, in particular when used in combination with the numbers and factors employed in the example calculations of the effective molar quantity of active species of the reaction modifier and the effective molar quantity of the hydrocarbons, as given hereinbefore.

It is preferred to operate in the post-break-through phase at the catalyst temperature $T_1$ employing such a value of $Q_1$ that the selectivity towards the olefin oxide formation is optimal. When this is the case, the epoxidation process will continue to operate at an optimum selectivity, but not necessarily the same selectivity, when employing the catalyst temperature $T_2$ and substantially the value of $Q_2$ as calculated in accordance with formula (I).

In the post-break-through phase, further reaction conditions may be selected from wide ranges, as set out hereinafter. The reactor inlet pressure is typically at most 2500 kPa absolute. The reactor inlet pressure is typically at least 1000 kPa absolute. Preferably, when the epoxidation process is carried out as a gas phase process involving a packed catalyst bed, the GHSV is in the range of from 500 to 10000 Nl/(l.h). Typically, then pressure and the GHSV will not be changed when leaving the break-through phase. Preferably, the work rate is in the range of from 0.5 to 10 kmole olefin oxide produced per m³ of catalyst per hour, in particular 0.7 to 8 kmole olefin oxide produced per m³ of catalyst per hour, for example 5 kmole olefin oxide produced per m³ of catalyst per hour. As used herein, the work rate is the amount of the olefin oxide produced per unit volume of catalyst per hour and the selectivity is the molar quantity of the olefin oxide formed relative to the molar quantity of the olefin converted.

The olefin oxide produced may be recovered from the reactor product by using methods known in the art, for example by absorbing the olefin oxide from a reactor outlet stream in water and optionally recovering the olefin oxide from the aqueous solution by distillation. At least a portion of the aqueous solution containing the olefin oxide may be applied in a subsequent process for converting the olefin oxide into a 1,2-diol or a 1,2-diol ether.

The olefin oxide produced in the present epoxidation process may be converted into a 1,2-diol, a 1,2-diol ether, or an alkanolamine. As this invention leads to a more attractive process for the production of the olefin oxide, it concurrently leads to a more attractive process which comprises producing the olefin oxide in accordance with the invention and the subsequent use of the obtained olefin oxide in the manufacture of the 1,2-diol, 1,2-diol ether and/or alkanolamine.

The conversion into the 1,2-diol or the 1,2-diol ether may comprise, for example, reacting the olefin oxide with water, suitably using an acidic or a basic catalyst. For example, for making predominantly the 1,2-diol and less 1,2-diol ether, the olefin oxide may be reacted with a ten fold molar excess of water, in a liquid phase reaction in presence of an acid catalyst, e.g. 0.5–1.0% w sulfuric acid, based on the total reaction mixture, at 50–70° C. at 1 bar absolute, or in a gas phase reaction at 130–240° C. and 20–40 bar absolute, preferably in the absence of a catalyst. If the proportion of water is lowered the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, such as methanol or ethanol, by replacing at least a portion of the water by the alcohol.

The conversion into the alkanolamine may comprise, for example, reacting the olefin oxide with ammonia. Anhydrous or aqueous ammonia may be used, although anhydrous ammonia is typically used to favour the production of monoalkanolamine. For methods applicable in the conversion of the olefin oxide into the alkanolamine, reference may be made to, for example U.S. Pat. No. 4,845,296, which is incorporated herein by reference.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The alkanolamine may be used, for example, in the treating ("sweetening") of natural gas.

Unless specified otherwise, the organic compounds mentioned herein, for example the olefins, 1,2-diols, 1,2-diol ethers and reaction modifiers, have typically at most 40 carbon atoms, more typically at most 20 carbon atoms, in particular at most 10. carbon atoms, more in particular at most 6 carbon atoms. As defined herein, ranges for numbers of carbon atoms (i.e. carbon number) include the numbers specified for the limits of the ranges.

The following examples will illustrate the invention, without limiting the scope of the invention.

EXAMPLES 1–3 (EXAMPLES 1 AND 2 ACCORDING TO THE INVENTION; EXAMPLE 3 FOR COMPARISON)

A catalyst, as defined in U.S. Pat. No. 4,766,105, comprising silver, rhenium and cesium on α-alumina, was employed in the following experiments.

Three identical tubular microreactors were charged each with a 4.2-g sample of the crushed catalyst. The catalysts in the reactors were heated at 215° C. during 40 hours under a flow of nitrogen gas at GHSV of 820 Nl/l.h. The catalyst temperatures were increased to 225° C., the nitrogen feed to the catalysts was replaced by a feed of an ethylene/carbon dioxide/nitrogen mixture, and subsequently ethyl chloride was added to the feed. Then oxygen was added to the feed. The oxygen/ethylene/carbon dioxide/nitrogen volume ratio in the resulting feed amounted to 4:15:4:77. The ethyl chloride concentration in the feed was 2.6 ppmv (i.e. $2.6 \times 10^{-4}$ mole-%, calculated as moles of chlorine, relative to the total feed). The relative quantity Q was $8.7 \times 10^{-6}$. The GHSV was 3300 Nl/l.h. The reactor inlet pressure was 1530 kPa absolute. These conditions were maintained for 2 hours.

Each of the catalysts was then subjected to temperatures, as set out in the following table.

| Step | Runhour | Catalyst temperature (° C.) | Ethyl chloride in feed (ppmv) | Time (h) |
|---|---|---|---|---|
| 1*) | 1 | 225 | 2.6 | 2 |
| 2 | 3 | 235 | 2.6 | 2 |
| 3 | 5 | **) | 2.6 | 8 |

*)The temperature increase to 225° C. defined the beginning of Runhour 1
**)The catalyst temperature was adjusted so as to obtain and maintain 3.1% v ethylene oxide in the reactor outlet stream Starting from Runhour 13, the catalysts were subjected to different temperatures and feed compositions as specified hereinafter.

Example 1 (according to the invention) involved a 5-hours heating at 270° C. (cf. step 14 hereinafter), as follows:

| Step | Runhour | Catalyst temperature (° C.) | Ethyl chloride in feed (ppmv) | Time (h) |
|---|---|---|---|---|
| 4 | 13 | 245 | 2.4 | 1 |
| 5 | 14 | 248 | 2.1 | 1 |
| 6 | 15 | 250 | 1.8 | 1 |
| 7 | 16 | 253 | 1.5 | 1 |
| 8 | 17 | 255 | 1.2 | 1 |
| 9 | 18 | 258 | 1.0 | 1 |
| 10 | 19 | 260 | 0.9 | 2 |
| 11 | 21 | 263 | 0.9 | 2 |
| 12 | 23 | 265 | 0.9 | 2 |
| 13 | 25 | 268 | 0.9 | 2 |
| 14 | 27 | 270 | 0.9 | 5 |
| 15 | 32 | 250 | 1.2*) | 2 |
| 16 | 34 | 250 | 1.8 | 2 |
| 17 | 36 | 250 | 2.2 | 2 |
| 18 | 38 | <250**) | 2.2 | 20 |
| 19 | 58 | <250**) | 2.6 | 16 |
| 20 | 74 | <250**) | 3.0 | 10 |
| 21 | 84 | <250**) | 2.6 | Hold |

*)The feed composition was changed to oxygen/ethylene/carbon dioxide/nitrogen volume ratio 8/30/2/60
**)The catalyst temperature was adjusted so as to maintain 3.1% v ethylene oxide in the reactor outlet stream; steps 12–14 involved an optimization of the selectivity at constant ethylene oxide content (3.1% v) in the reactor outlet stream Example 2 (according to the invention) was carried out as Example 1, except for the application of an ethyl chloride concentration of 3.0 ppmv in steps 4–14.

Example 3 (for comparison) involved a 48-hours heating at 260° C. (cf. step 14 hereinafter), as follows:

| Step | Runhour | Catalyst temperature (° C.) | Ethyl chloride in feed (ppmv) | Time (h) |
|---|---|---|---|---|
| 4 | 13 | 245 | 2.4 | 1 |
| 5 | 14 | 248 | 2.1 | 1 |
| 6 | 15 | 250 | 1.8 | 1 |
| 7 | 16 | 253 | 1.5 | 1 |
| 8 | 17 | 255 | 1.2 | 1 |
| 9 | 18 | 258 | 1.0 | 1 |
| 10 | 19 | 260 | 0.9 | 48 |
| 11–17 | 67 | As in steps 15–21 of Example 1 | | |

The three catalysts exhibited similar performance in selectivity and activity in steps 21 of Examples 1 and 2 and step 17 of Example 3, as in these Examples the same catalyst temperature (about 246° C.) and the same concentration of ethyl chloride in the feed led to approximately the similar work rates and selectivities (about 86.5%-mole).

Figure 1:
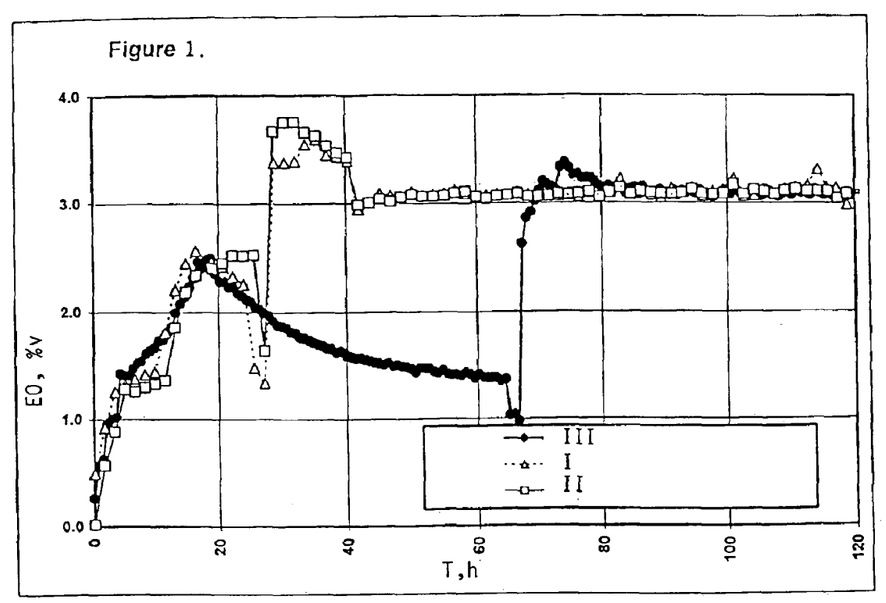
FIG. 1 shows the concentration of ethylene oxide in a reactor outlet stream ("EO, % v") in % v, relative to the total outlet stream, as a function of the Runhour ("T, h"), as observed in Example 1 ("I"), Example 2 ("II") and Example 3 ("III"), hereinafter.

Reference is made to FIG. 1. The FIGURE shows that in Example 1 and, in particular, in Example 2 (at a higher ethyl chloride concentration), in the time span from Runhour 27 to Runhour 43 there was a higher than targeted ethylene oxide production, followed by the targeted production from Runhour 43 (in these Examples the targeted ethylene oxide production is represented by 3.1% v ethylene oxide in the reactor outlet stream). The corresponding higher than targeted ethylene oxide production effect was substantially smaller in Example 3, Runhours 69–81, and the targeted production started at Runhour 81. FIG. 1 also shows that in Example 3 during the break-through phase 48 hours at 260° C. were needed for the catalyst to stabilise the ethylene production under the prevailing circumstances (from Runhours 19 to 27), and during these Runhours the ethylene oxide production was substantially below the target production, whereas in Examples 1 and 2 the corresponding period lasted only 5 hours (at 270° C.). This resulted in a higher overall ethylene oxide production in Examples 1 and 2, compared with Example 3: at Runhour 120 the cumulative ethylene oxide production was about 24 T/m$^3$ catalyst in Example 1 and 2, but it was about 19 T/m$^3$ catalyst in Example 3.

What is claimed:

1. A method for the start-up of a process for the epoxidation of an olefin, which method comprises the steps of
   contacting a packed catalyst bed comprising a silver-based highly selective epoxidation catalyst, or a precursor of the catalyst comprising the silver in cationic form, with a feed comprising oxygen at a temperature of the catalyst bed above 260° C. for a period of at most 150 hours, and
   subsequently decreasing the temperature of the catalyst bed to a value of at most 260° C.

2. A method as claimed in claim 1, wherein the catalyst, or the precursor of the catalyst, comprises, in addition to silver, a Group IA metal, and one or more selectivity enhancing dopants selected from rhenium, molybdenum, and tungsten.

3. A method as claimed in claim 2, wherein the catalyst, or the precursor of the catalyst, comprises, in addition to silver, rhenium or compound thereof, a further metal or compound thereof selected from the group of Group IA metals, Group IIA metals, molybdenum, tungsten, chromium, titanium, hafnium, zirconium, vanadium, thallium, thorium, tantalum, niobium, gallium and germanium and mixtures thereof, on a support material.

4. A method as claimed in claim 3, wherein the catalyst, or the precursor of the catalyst, comprises, in addition, a rhenium co-promoter selected from one or more of sulfur, phosphorus, boron, and compounds thereof.

5. A method as claimed in claim 1, wherein the catalyst, or the precursor of the catalyst, comprises silver in a quantity in the range of from 0.01 to 0.22 g/m², relative to the surface area of the support.

6. A method as claimed in claim 5, wherein the catalyst, or the precursor of the catalyst, comprises silver in a quantity in the range of from 0.02 to 0.2 g/m², relative to the surface area of the support.

7. A method as claimed in claim 1, wherein the temperature above 260° C. is in the range of from 260 to 290° C.

8. A method as claimed in claim 7, wherein the temperature above 260° C. is in the range of from 265 to 280° C.

9. A method as claimed in claim 1, wherein the catalyst temperature is maintained above 260° C. for a period of from 1 to 30 hours.

10. A method as claimed in claim 9, wherein the catalyst temperature is maintained above 260° C. for a period of from 2 to 20 hours.

11. A method as claimed in claim 1, wherein the feed comprises in addition an olefin in a quantity of from 5 to 70 mole-%; a saturated hydrocarbon, if any, in a quantity of from 0 to 70 mole-%; and oxygen in a quantity of from 0.5 to 15 mole-%, relative to the total feed.

12. A method as claimed in claim 11, wherein the feed comprises the olefin in a quantity of from 10 to 50 mole-%; the saturated hydrocarbon in a quantity of from 10 to 60 mole-%; and oxygen in a quantity of from 1 to 12 mole-%, relative to the total feed.

13. A method as claimed in claim 11, wherein the olefin is ethylene.

14. A method as claimed in claim 11, wherein the feed comprises in addition an organic halide, at a concentration in the range of from $1 \times 10^{-4}$ to $30 \times 10^{-4}$ mole-%, calculated on the basis of the halogen content, relative to the total feed.

15. A method as claimed in claim 14, wherein the organic halide is an chlorohydrocarbon, present at a concentration in the range of from $1.5 \times 10^{-4}$ to $20 \times 20^{-4}$ mole-%, calculated on the basis of the halogen content, relative to the total feed.

16. A method as claimed in claim 1, wherein the method is practiced as a gas phase process involving a packed catalyst bed and wherein during the step of contacting the feed with the catalyst, or the precursor of the catalyst, at a temperature above 260° C., a reactor inlet pressure is in the range of from 1000 to 2500 kPa absolute, and a Gas Hourly Space Velocity in the range of from 500 to 10000 Nl/(l.h).

17. A method as claimed in claim 1, wherein prior to the step of contacting the feed with the catalyst, or the precursor of the catalyst, at a temperature above, 260° C., the catalyst is contacted with the feed comprising the olefin, or the olefin and a saturated hydrocarbon, at a temperature of at most 260° C., and subsequently an organic halide is added to the feed and oxygen is added to the feed.

18. A method as claimed in claim 17, wherein prior to the step of contacting the feed with the catalyst, or the precursor of the catalyst, at a temperature above 260° C., the catalyst is contacted with the feed comprising ethylene and methane, at a temperature in the range of from 200 to 250° C., subsequently the organic halide is added to the feed, and thereafter oxygen is added to the feed.

19. A method as claimed in claim 17, wherein the catalyst, or the precursor of the catalyst, is applied as a packed bed positioned in a reactor, and the organic halide is detected in a reactor outlet stream before oxygen is added to the feed.

20. A method as claimed in claim 17, wherein oxygen is added to the feed simultaneously with the organic halide.

21. A method as claimed in claim 17, wherein after the addition of the organic halide and oxygen to the feed, the feed comprises the olefin in a quantity of from 5 to 70 mole-%; the saturated hydrocarbon, if any, in a quantity of from 0 to 70 mole-%; and oxygen in a quantity of from 0.5 to 15 mole-%, relative to the feed.

22. A method as claimed in claim 21, wherein the feed comprises the olefin in a quantity of from 10 to 50 mole-%; the saturated hydrocarbon in a quantity of from 10 to 60 mole-%; and oxygen in a quantity of from 1 to 12 mole-%, relative to the feed.

23. A method for the start-up of a process for the epoxidation of an olefin, which method comprises the steps of contacting a packed catalyst bed comprising a silver-based highly selective epoxidation catalyst, or a precursor of the catalyst comprising the silver in cationic form, with a feed comprising oxygen at a temperature of the catalyst bed above 260° C. for a period of at most 150 hours, and subsequently decreasing the temperature of the catalyst bed to a value of at most 260° C. and contacting the catalyst with the feed comprising the olefin and oxygen.

24. A process as claimed in claim 23, wherein in the step in which the temperature of the catalyst bed is decreased to a value of at most 260° C., the feed comprises the olefin in a concentration in the range of from 5 to 70 mole-%; oxygen in a concentration in the range of from 1 to 15 mole-%; and a saturated hydrocarbons, if any, in a quantity of up to 70 mole-%, relative to the total feed.

25. A process as claimed in claim 24, wherein the feed comprises the olefin in a concentration in the range of from 10 to 50 mole-%; oxygen in a concentration in the rang of from 2 to 12 mole-%; and a saturated hydrocarbons in a quantity of from 10 to 60 mole-%, relative to the total feed.

26. A process as claimed in claim 23, wherein during the step of contacting the feed with the catalyst, or the precursor of the catalyst, at a temperature above 260° C., the feed comprises oxygen and, in addition, the olefin at a lower concentration of oxygen and a lower concentration of the olefin compared with the feed applied in the step in which the temperature of the catalyst bed is decreased to a value of at most 260° C.

27. A process as claimed in, claim 23, wherein during the step of contracting the feed with the catalyst, or the precursor of the catalyst, at a temperature above 260° C., the feed comprises oxygen and, in addition, the olefin at a lower concentration of oxygen and a lower concentration of the olefin compared with the feed applied in the step in which the temperature of the catalyst bed is decreased to a value of at most 260° C.

28. A process as claimed in claim 23, wherein the olefin is ethylene.

29. A process as claimed in claim 23, wherein the feed comprising the olefin and oxygen comprises in addition an organic chloride and optionally a nitrate- or nitrite- forming compound.

30. A process as claimed in claim 23, wherein in the step in which the temperature of the catalyst bed is decreased to a value of at most 260° C., the temperature is decreased to a temperature in the range of from 180 to 260° C.

31. A process as claimed in claim 30, wherein in the step in which the temperature of the catalyst bed is decreased to a value of at most 260° C., the temperature is decreased to a temperature in the range of from 200 to 233° C.

32. A process as claimed in claim 30, wherein subsequently to decreased the temperature of the catalyst bed to a value in the range of from 180 to 260° C., the temperature is increased to a value above 260° C.

33. A process as claimed in claim 32, wherein the temperature is increased to a value up to a temperature of 325° C.

34. A process as claimed in claim 33, wherein the temperature is increased to a value up to the range of from 270 to 300° C.

35. A process for making a 1,2-diol, a 1,2-diol ether or an alkanolamine comprising converting an olefin oxide into the 1,2-diol, the 1,2-diol ether or the alkanolamine, wherein the olefin oxide has been obtained by a process for the epoxidation of an olefin according to claim 23.

* * * * *